US009825455B2

(12) United States Patent
Sandhu et al.

(10) Patent No.: US 9,825,455 B2
(45) Date of Patent: Nov. 21, 2017

(54) SYSTEM AND METHOD OF AUTOMATIC DETECTION AND PREVENTION OF MOTOR RUNAWAY

(71) Applicant: St. Jude Medical, Atrial Fibrillation Division, Inc., St. Paul, MN (US)

(72) Inventors: Kulbir S. Sandhu, Singapore (SG); Atila Amiri, Fremont, CA (US); Otto Chiu, Fremont, CA (US); Samuel Gee, San Bruno, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 130 days.

(21) Appl. No.: 14/283,991

(22) Filed: May 21, 2014

(65) Prior Publication Data
US 2014/0340796 A1 Nov. 20, 2014

Related U.S. Application Data

(63) Continuation of application No. 12/970,534, filed on Dec. 16, 2010, now Pat. No. 8,736,212.

(51) Int. Cl.
*H02P 1/00* (2006.01)
*H02P 7/00* (2016.01)
(Continued)

(52) U.S. Cl.
CPC .......... *H02H 7/0833* (2013.01); *A61B 34/30* (2016.02); *H02H 7/097* (2013.01);
(Continued)

(58) Field of Classification Search
CPC ......... H02H 7/0833; H02H 7/085; H02P 7/29
(Continued)

(56) References Cited

U.S. PATENT DOCUMENTS 6,233,476 B1  5/2001  Strommer et al.
6,233,504 B1  5/2001  Das et al.
(Continued)

FOREIGN PATENT DOCUMENTS

EP        0072866      3/1983
JP        S63170706    7/1988
(Continued)

OTHER PUBLICATIONS

International Search Report and Written Opinion for PCT Application No. PCT/US2011/049313, dated Jan. 6, 2012, 8 pages.
(Continued)

*Primary Examiner* — Bentsu Ro
*Assistant Examiner* — Gabriel Agared
(74) *Attorney, Agent, or Firm* — Dykema Gossett PLLC

(57) ABSTRACT

A robotic catheter control system includes a plurality of electric motors. Diagnostic logic automatically detects motor runaway fault conditions based on the current motor position, the target motor position and a predetermined tolerance parameter. Fault conditions include overshoot, movement in the a non-prescribed direction, exceeding a prescribed maximum motor speed and exceeding a prescribed maximum motor acceleration. The diagnostic logic terminates operating power to the electric motor when a fault condition is detected for any one of the motor. An error message is generated to notify the operator of the fault.

15 Claims, 10 Drawing Sheets

(51) Int. Cl.
    *G05B 23/02* (2006.01)
    *H02H 7/08* (2006.01)
    *H02H 7/097* (2006.01)
    *A61B 18/14* (2006.01)
    *A61B 17/00* (2006.01)
    *A61B 34/30* (2016.01)
    *A61B 34/20* (2016.01)

(52) U.S. Cl.
    CPC .. *A61B 18/1492* (2013.01); *A61B 2017/00123* (2013.01); *A61B 2034/2051* (2016.02); *A61B 2034/301* (2016.02)

(58) Field of Classification Search
    USPC .......................... 318/434, 565, 568.4, 568.24
    See application file for complete search history.

(56) References Cited

U.S. PATENT DOCUMENTS

| | | | |
|---|---|---|---|
| 6,690,963 B2 | 2/2004 | Ben-Haim et al. | |
| 6,859,660 B2 | 2/2005 | Vilsmeier | |
| 7,043,338 B2* | 5/2006 | Jinno | B25J 3/04 |
| | | | 600/130 |
| 7,157,875 B2* | 1/2007 | Kamen | A63C 17/12 |
| | | | 310/112 |
| 7,197,354 B2 | 3/2007 | Sobe | |
| 7,263,397 B2 | 8/2007 | Hauck et al. | |
| 7,301,296 B1* | 11/2007 | Discenzo | G05B 19/4063 |
| | | | 318/400.01 |
| 7,386,339 B2 | 6/2008 | Strommer et al. | |
| 7,536,218 B2 | 5/2009 | Govari et al. | |
| 7,848,789 B2 | 12/2010 | Govari et al. | |
| 7,905,234 B2* | 3/2011 | Jinno | A61B 17/00234 |
| | | | 128/898 |
| 2007/0197896 A1* | 8/2007 | Moll | A61B 1/00039 |
| | | | 600/407 |
| 2008/0249536 A1 | 10/2008 | Stahler | |
| 2008/0275428 A1 | 11/2008 | Tegg | |
| 2009/0012533 A1 | 1/2009 | Barbagli et al. | |
| 2009/0163904 A1 | 6/2009 | Miller et al. | |
| 2009/0177095 A1 | 7/2009 | Aeby et al. | |
| 2009/0247942 A1 | 10/2009 | Kirschenman | |
| 2009/0247943 A1 | 10/2009 | Kirschenman | |
| 2009/0247944 A1 | 10/2009 | Kirschenman et al. | |
| 2009/0247993 A1 | 10/2009 | Kirschenman et al. | |
| 2009/0248042 A1 | 10/2009 | Kirschenman | |
| 2009/0259340 A1* | 10/2009 | Umemoto | A61B 1/0051 |
| | | | 700/275 |
| 2009/0275827 A1 | 11/2009 | Aiken et al. | |
| 2010/0079099 A1* | 4/2010 | Katsuki | G05B 23/0256 |
| | | | 318/565 |
| 2010/0204713 A1 | 8/2010 | Ruiz Morales | |
| 2010/0256558 A1 | 10/2010 | Olson et al. | |
| 2011/0015569 A1 | 1/2011 | Kirschenman et al. | |
| 2011/0022045 A1 | 1/2011 | Cao et al. | |

FOREIGN PATENT DOCUMENTS

| | | |
|---|---|---|
| JP | 2000218577 | 8/2000 |
| WO | 2009120982 | 10/2009 |
| WO | 2010036746 | 4/2010 |

OTHER PUBLICATIONS

Stoy, Kasper, et al. "Modular Robots: The State of the Art", IEEE International Conference on Robotics and Automation Workshop, May 3, 2010, pp. 1-121.

Supplementary European Search Report for EP Application No. 11849340.2 dated Apr. 10, 2015, 7 pages.

* cited by examiner

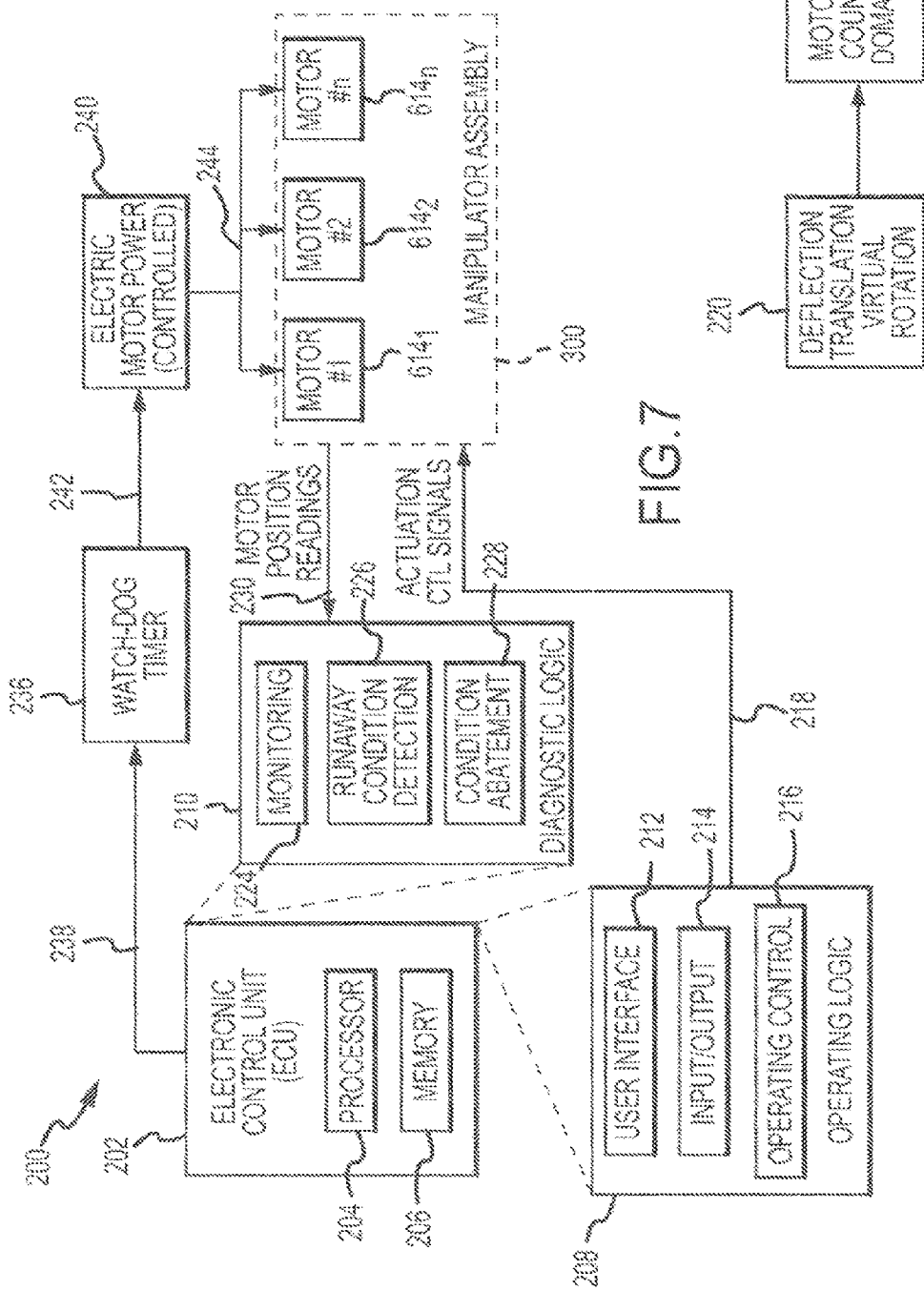

SYSTEM AND METHOD OF AUTOMATIC DETECTION AND PREVENTION OF MOTOR RUNAWAY

CROSS-REFERENCE TO RELATED APPLICATIONS

This application is a continuation of U.S. application Ser. No. 12/970,534, filed 16 Dec. 2010 now pending, which is each hereby incorporated by reference as though fully set forth herein.

BACKGROUND OF THE INVENTION a. Field of the Invention

The present disclosure relates generally to a fault detection and abatement system, and more particularly to a system and method of automatic detection and prevention of motor runaway.

b. Background Art

Electrophysiology (EP) catheters are used in a variety of diagnostic and/or therapeutic medical procedures to correct conditions such as atrial arrhythmia, including for example, ectopic atrial tachycardia, atrial fibrillation, and atrial flutter. Arrhythmia can create a variety of dangerous conditions including irregular heart rates, loss of synchronous atrioventricular contractions and stasis of blood flow which can lead to a variety of ailments.

In a typical EP procedure, a physician manipulates a catheter through a patient's vasculature to, for example, a patient's heart. The catheter typically carries one or more electrodes that may be used for mapping, ablation, diagnosis, and the like. Once at the target tissue site, the physician commences diagnostic and/or therapeutic procedures, for example, ablative procedures such as radio frequency (RF), microwave, cryogenic, laser, chemical, acoustic/ultrasound or high-intensity focused ultrasound (HIFU) ablation, to name a few different sources of ablation energy. The resulting lesion, if properly located and sufficiently contiguous with other lesions, disrupts undesirable electrical pathways and thereby limits or prevents stray electrical signals that can lead to arrhythmias. Such procedures require precise control of the catheter during navigation to and delivery of therapy to the target tissue site, which can invariably be a function of a user's skill level.

Robotic catheter systems are known to facilitate such precise control. Robotic catheter systems generally carry out (as a mechanical surrogate) input commands of a clinician or other end-user to deploy, navigate and manipulate a catheter and/or an introducer or sheath for a catheter or other elongate medical instrument, for example, a robotic catheter system described, depicted, and/or claimed in U.S. application Ser. No. 12/347,811 entitled "ROBOTIC CATHETER SYSTEM" owned by the common assignee of the present disclosure and hereby incorporated by reference in its entirety. Such robotic catheter systems include a variety of actuation mechanisms, such as electric motors, for controlling translation and deflection of the catheter and associated sheath. A malfunction in one or more of the motors (e.g., a runaway condition) may result in an unexpected and/or undesirable movement or stoppage of movement of the catheter or sheath.

Motor runaway (i.e., a motor fault condition) may manifest itself with the motor moving in the "wrong" direction (i.e., moving away from its current position in a direction opposite that needed to reach the prescribed target position). In addition, the motor may overshoot the prescribed target position, even though going in the correct direction. There are many reasons that these and other fault conditions can occur, including, for example, motor "over current", noise issues, motor firmware anomalies as well as owing to the mechanical characteristics of the motors themselves. While knowing the root cause of these fault conditions may be useful in overall system design (e.g., to avoid the occurrence of the faults in the first place), there nonetheless remains a need to detect and abate such fault conditions when they occur.

There is therefore a need for a system and method that minimizes or eliminates one or more problems as set forth above.

BRIEF SUMMARY OF THE INVENTION

One advantage of the methods and apparatus described, depicted and claimed herein relates to the ability to detect a number of different fault conditions indicative of motor runaway in a robotic catheter system and to effectively abate such fault. Another advantage involves a diagnostic that operates substantially continuously such that a motor runaway fault condition will not go undetected for more than a predetermined amount of time. A still further advantage relates to a software-based implementation, reducing external hardware components and thereby reducing cost and complexity.

The disclosure is directed to an apparatus for use in a robotic control system for manipulating a medical device, such as a catheter or a sheath, that is able to detect and abate motor runaway fault conditions. The apparatus includes an electronic control unit (ECU) and a memory coupled to the ECU, and logic stored in the memory configured to be executed by the ECU. The logic includes a diagnostic module that is configured to monitor operation of a plurality of electrically-operated actuation units of the robotic control system where the actuation units are operative to manipulate the medical device. The diagnostic module is further configured to detect when a predetermined fault condition associated with at least one of the actuation units occurs. Advantageously, the diagnostic module is further configured to abate the fault condition, for example, by terminating operating power supplied to the actuation units. In an embodiment, the actuation units may be electrically-operated motors, and where the diagnostic module determines the existence of a fault by assessing, for each motor, a respective current motor position, a respective prescribed target motor position, and a predetermined tolerance parameter.

The predetermined fault condition, in an embodiment where the actuation units comprise electric motors, may be selected from the group comprising (i) a first condition when at least one of the motors rotate in a direction opposite that of a commanded direction; (ii) a second condition when at least one of the motors has rotated to an actual position short of or beyond a commanded position by at least a predetermined amount; (iii) a third condition when a speed of at least one motor exceeds a respective maximum speed threshold; and (iv) a fourth condition when a rate of change of the speed of at least one motor exceeds a respective maximum acceleration threshold.

In another aspect, a robotic control and guidance system is provided for manipulating a medical device. The robotic system includes an electronic control unit (ECU), a memory coupled to the ECU, and logic stored in the memory configured to be executed by the ECU. The logic includes an operating module and a diagnostic module. The robot system further includes a manipulator assembly including a plurality of electrically-operated actuation units configured to actuate one or more control members of the medical device in response to a plurality of actuation control signals. In an embodiment, the actuation units may comprise electric motors. The operating module is configured to produce the actuation control signals so as to manipulate the medical device in accordance with a predetermined operating strategy. In an embodiment, the actuation control signals are further determined based on a type of desired motion associated with the medical device (e.g., translation, deflection, virtual rotation). The diagnostic module is configured to monitor the operation of the actuation units and detect when a predetermined fault condition occurs. The diagnostic module is configured to abate the fault condition when detected, for example, by terminating the operating power supplied to the actuation units.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIG. 7 is a diagrammatic and block diagram view of the electronic control system of FIG. 1, having motor runaway fault detection logic.

FIG. 8 is a block diagram showing, in simplified form, a relationship between commanded catheter and sheath movements and motor actuation movements.

DETAILED DESCRIPTION OF THE INVENTION

Before proceeding to a detailed description of a system and method for motor runaway fault detection, a brief overview (for context) of an exemplary robotic control and guidance system (RCGS) will first be described. In particular, the description of the RCGS will detail how several (i.e., ten) electric motors may be used to control the translation, distal bending and virtual rotation of a catheter and surrounding sheath. After the RCGS, the present specification will then describe diagnostic logic used to detect motor runaway fault conditions and how such fault conditions may be abated (i.e., how the diagnostic methods and systems of the present invention may be applied to an RCGS).

Figure 1:
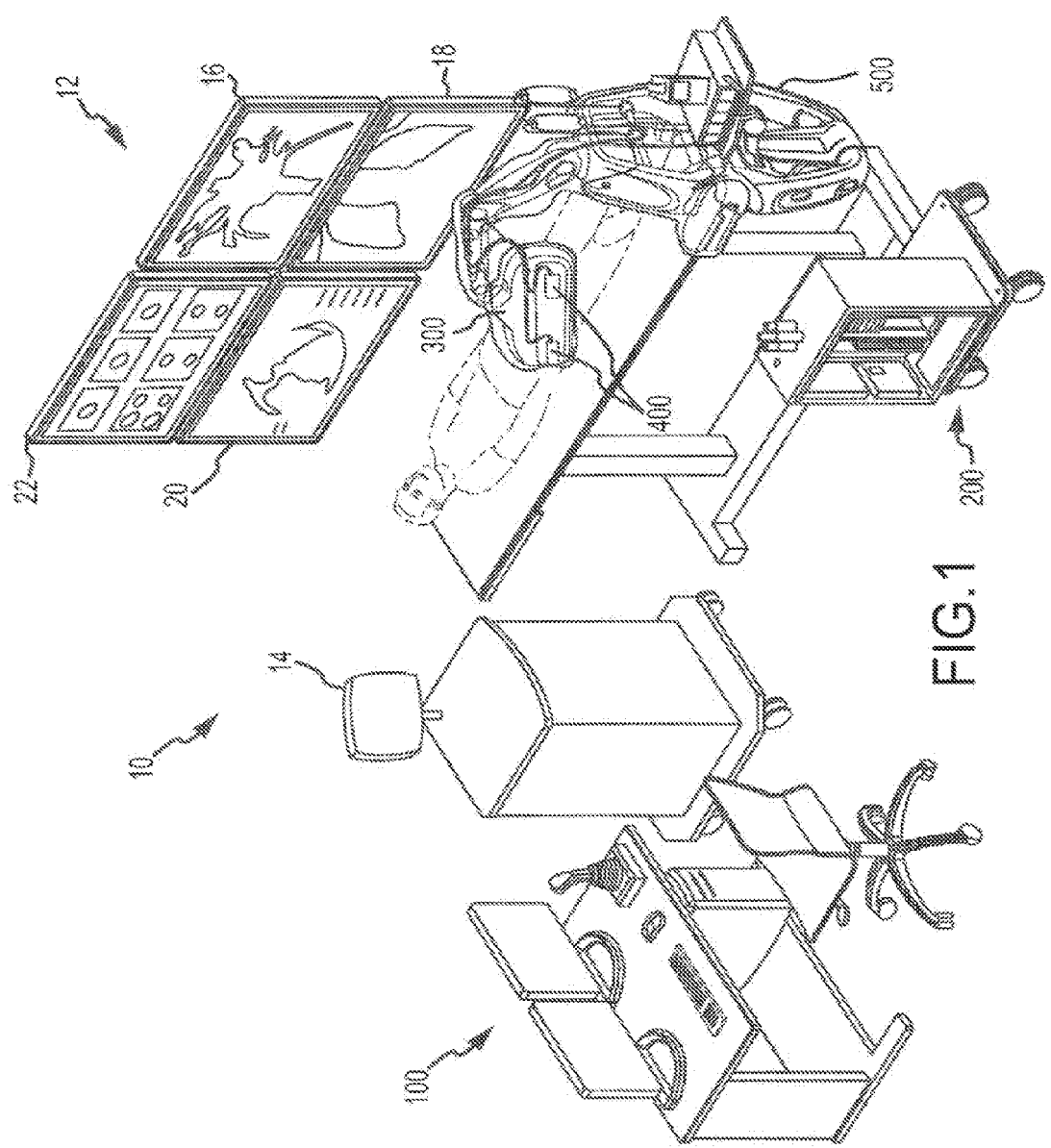
FIG. 1 is an isometric diagrammatic view of a robotic catheter system, illustrating an exemplary layout of various system components.

In this regard, and now referring to the drawings wherein like reference numerals are used to identify identical components in the various views, FIG. 1 is a diagrammatic view of an exemplary RCGS 10, in which several aspects of a system and method for automatic detection and prevention of motor runaway may be used.

Exemplary RCGS System Description.

RCGS 10 can be likened to power steering for a catheter system. The RCGS 10 can be used, for example, to manipulate the location and orientation of catheters and sheaths in a heart chamber or in another body cavity or lumen. The RCGS 10 thus provides the user with a similar type of control provided by a conventional manually-operated system, but allows for repeatable, precise, and dynamic movements. For example, a user such as an electrophysiologist can identify locations (potentially forming a path) on a rendered computer model of the cardiac anatomy. The system can be configured to relate those digitally selected points to positions within a patient's actual/physical anatomy, and can thereafter command and control the movement of the catheter to the defined positions. Once at the specified target position, either the user or the system can perform the desired diagnostic or therapeutic function. The RCGS 10 enables full robotic navigation/guidance and control.

As shown in FIG. 1, the RCGS 10 can generally include one or more monitors or displays 12, a visualization, mapping and navigation (including localization) system 14, a human input device and control system (referred to as "input control system") 100, an electronic control system 200, a manipulator assembly 300 for operating a device cartridge 400, and a manipulator support structure 500 for positioning the manipulator assembly 300 in proximity to a patient or a patient's bed.

Displays 12 are configured to visually present to a user information regarding patient anatomy, medical device location or the like, originating from a variety of different sources. Displays 12 can include (1) an ENSITE VELOCITY™ monitor 16 (coupled to system 14—described more fully below) for displaying cardiac chamber geometries or models, displaying activation timing and voltage data to identify arrhythmias, and for facilitating guidance of catheter movement; (2) a fluoroscopy monitor 18 for displaying a real-time x-ray image or for assisting a physician with catheter movement; (3) an intra-cardiac echo (ICE) display 20 to provide further imaging; and (4) an EP recording system display 22.

The system 14 is configured to provide many advanced features, such as visualization, mapping, navigation support and positioning (i.e., determine a position and orientation (P&O) of a sensor-equipped medical device, for example, a P&O of a distal tip portion of a catheter. Such functionality can be provided as part of a larger visualization, mapping and navigation system, for example, an ENSITE VELOCITY system running a version of NavX™ software commercially available from St. Jude Medical, Inc., of St. Paul, Minn. and as also seen generally by reference to U.S. Pat. No. 7,263,397 entitled "METHOD AND APPARATUS FOR CATHETER NAVIGATION AND LOCATION AND MAPPING IN THE HEART" to Hauck et al., owned by the common assignee of the present disclosure, and hereby incorporated by reference in its entirety. System 14 can comprise conventional apparatus known generally in the art, for example, the ENSITE VELOCITY system described above or other known technologies for locating/navigating a catheter in space (and for visualization), including for example, the CARTO visualization and location system of Biosense Webster, Inc., (e.g., as exemplified by U.S. Pat. No. 6,690,963 entitled "System for Determining the Location and Orientation of an Invasive Medical Instrument" hereby incorporated by reference in its entirety), the AURORA® system of Northern Digital Inc., a magnetic field based localization system such as the gMPS system based on technology from MediGuide Ltd. of Haifa, Israel and now owned by St. Jude Medical, Inc. (e.g., as exemplified by U.S. Pat. Nos. 7,386,339, 7,197,354 and 6,233,476, all of which are hereby incorporated by reference in their entireties) or a hybrid magnetic field-impedance based system, such as the CARTO 3 visualization and location system of Biosense Webster, Inc. (e.g., as exemplified by U.S. Pat. No. 7,536, 218, and 7,848,789 both of which are hereby incorporated by reference in its entirety). Some of the localization, navigation and/or visualization systems can involve providing a sensor for producing signals indicative of catheter location and/or orientation information, and can include, for example one or more electrodes in the case of an impedance-based localization system such as the ENSITE VELOCITY system running NavX software, which electrodes can already exist in some instances, or alternatively, one or more coils (i.e., wire windings) configured to detect one or more characteristics of a low-strength magnetic field, for example, in the case of a magnetic-field based localization system such as the gMPS system using technology from MediGuide Ltd. described above.

The input control system 100 is configured to allow a user, such as an electrophysiologist, to interact with the RCGS 10, in order to control the movement and advancement/withdrawal of both a catheter and sheath (see, e.g., commonly assigned U.S. patent application Ser. No. 12/751,843 filed Mar. 31, 2010 entitled "ROBOTIC CATHETER SYSTEM" and PCT/US2009/038597 entitled "ROBOTIC CATHETER SYSTEM WITH DYNAMIC RESPONSE", published as WO 2009/120982; the entire disclosure of both applications being hereby incorporated by reference). Generally, several types of input devices and related controls can be employed, including, without limitation, instrumented traditional catheter handle controls, oversized catheter models, instrumented user-wearable gloves, touch screen display monitors, 2-D input devices, 3-D input devices, spatially detected styluses, and traditional joysticks. For a further description of exemplary input apparatus and related controls, see, for example, commonly assigned U.S. patent application Ser. No. 12/933,063 entitled "ROBOTIC CATHETER SYSTEM INPUT DEVICE" and U.S. patent application Ser. No. 12/347,442 entitled "MODEL CATHETER INPUT DEVICE", the entire disclosure of both applications being hereby incorporated by reference. The input devices can be configured to directly control the movement of the catheter and sheath, or can be configured, for example, to manipulate a target or cursor on an associated display.

The electronic control system 200 is configured to translate (i.e., interpret) inputs (e.g., motions) of the user at an input device or from another source into a resulting movement of the catheter and/or surrounding sheath. In this regard, the system 200 includes a programmed electronic control unit (ECU) in communication with a memory or other computer readable media (memory) suitable for information storage. Relevant to the present disclosure, the electronic control system 200 is configured, among other things, to issue commands (i.e., actuation control signals) to the manipulator assembly 300 (i.e., to the actuation units—electric motors) to move or bend the catheter and/or sheath to prescribed positions and/or in prescribed ways, all in accordance with the received user input and a predetermined operating strategy programmed into the system 200. In addition to the instant description, further details of a programmed electronic control system can be found in commonly assigned U.S. patent application Ser. No. 12/751, 843 filed Mar. 31, 2010 entitled "ROBOTIC CATHETER SYSTEM", described above. It should be understood that although the exemplary ENSITE VELOCITY System 14 and the electronic control system 200 are shown separately, integration of one or more computing functions can result in a system including an ECU on which can be run both (i) various control and diagnostic logic pertaining to the RCGS 10 and (ii) the visualization, mapping and navigation functionality of system 14.

The manipulator assembly 300, in response to such commands, is configured to maneuver the medical device (e.g., translation movement, such as advancement and withdrawal of the catheter and/or sheath), as well as to effectuate distal end (tip) deflection and/or rotation or virtual rotation. In an embodiment, the manipulator assembly 300 can include actuation mechanisms/units (e.g., a plurality of electric motor and lead screw combinations, or other electric motor configurations, as detailed below) for linearly actuating one or more control members (e.g., steering wires) associated with the medical device for achieving the above-described translation, deflection and/or rotation (or virtual rotation). In addition to the description set forth herein, further details of a manipulator assembly be can be found in commonly assigned U.S. patent application Ser. No. 12/347,826 titled "ROBOTIC CATHETER MANIPULATOR ASSEMBLY", the entire disclosure of which is hereby incorporated by reference.

A device cartridge 400 is provided for each medical device controlled by the RCGS 10. For this exemplary description of an RCGS, one cartridge is associated with a catheter and a second cartridge is associated with an outer sheath. The cartridge is then coupled, generally speaking, to the RCGS 10 for subsequent robotically-controlled movement. In addition to the description set forth herein, further details of a device cartridge can be found in commonly owned U.S. patent application Ser. No. 12/347,835 entitled "ROBOTIC CATHETER DEVICE CARTRIDGE" and U.S. patent application Ser. No. 12/347,842 "ROBOTIC CATHETER ROTATABLE DEVICE CARTRIDGE", the entire disclosure of both applications being hereby incorporated by reference.

Figure 2:
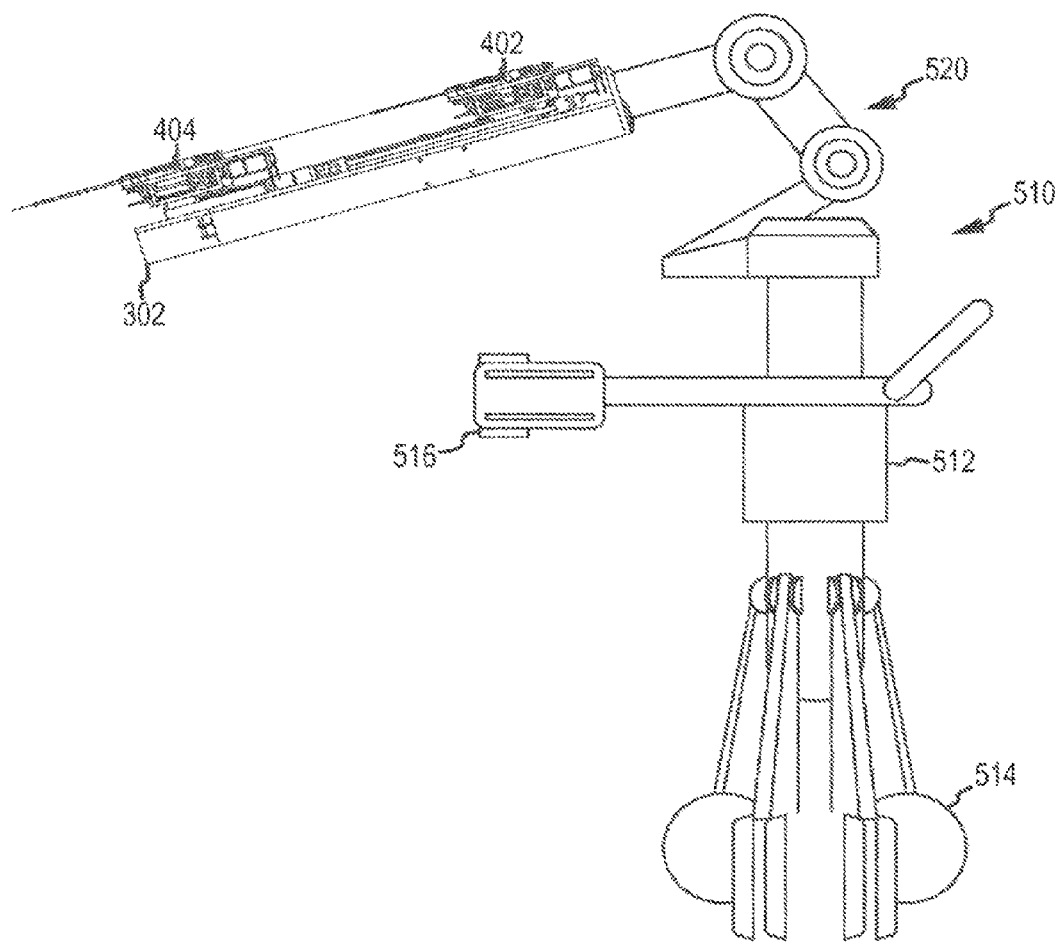
FIG. 2 is a side view of a manipulator assembly shown in FIG. 1, coupled to a robotic support structure, showing side views of catheter and sheath manipulation mechanisms.

FIG. 2 is a side view of an exemplary robotic catheter manipulator support structure, designated structure 510 (see commonly owned U.S. patent application Ser. No. 12/347, 811 entitled "ROBOTIC CATHETER SYSTEM" described above). The structure 510 can generally include a support frame 512 including retractable wheels 514 and attachment assembly 516 for attachment to an operating bed (not shown). A plurality of support linkages 520 can be provided for accurately positioning one or more manipulator assemblies, such as manipulator assembly 302. The assembly 302 is configured to serve as the interface for the mechanical control of the movements or actions of one or more device cartridges, such as catheter and sheath cartridges 402, 404 described below. Each device cartridge is configured to receive and retain a respective proximal end of an associated medical device (e.g., catheter or sheath). The assembly 302 also includes a plurality of manipulation bases onto which the device cartridges are mounted. After mounting, the manipulator assembly 302, through the manipulation bases, is capable of manipulating the attached catheter and sheath.

Figure 3A:
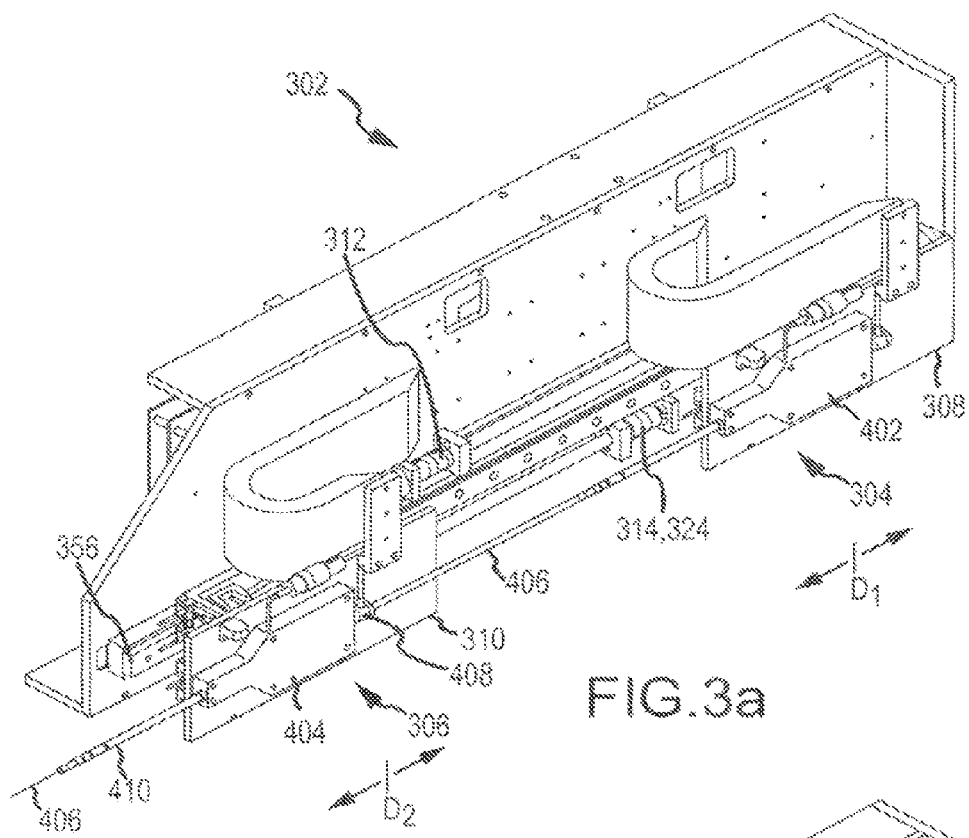
FIGS. 3a-3b are isometric views of a manipulator assembly shown in FIG. 2, showing the catheter and sheath manipulation mechanism in greater detail.
Figure 3B:
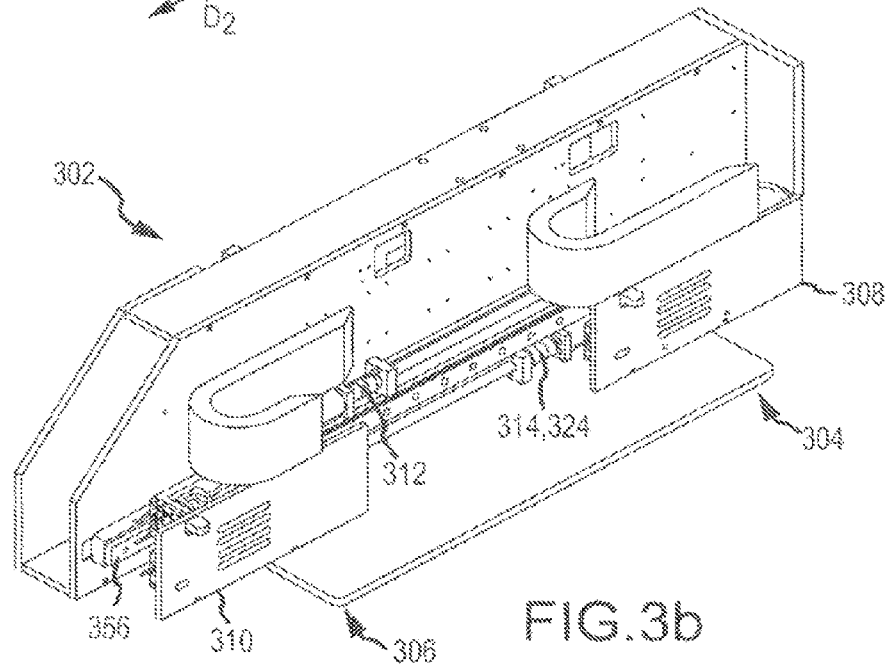
Figure 4A:
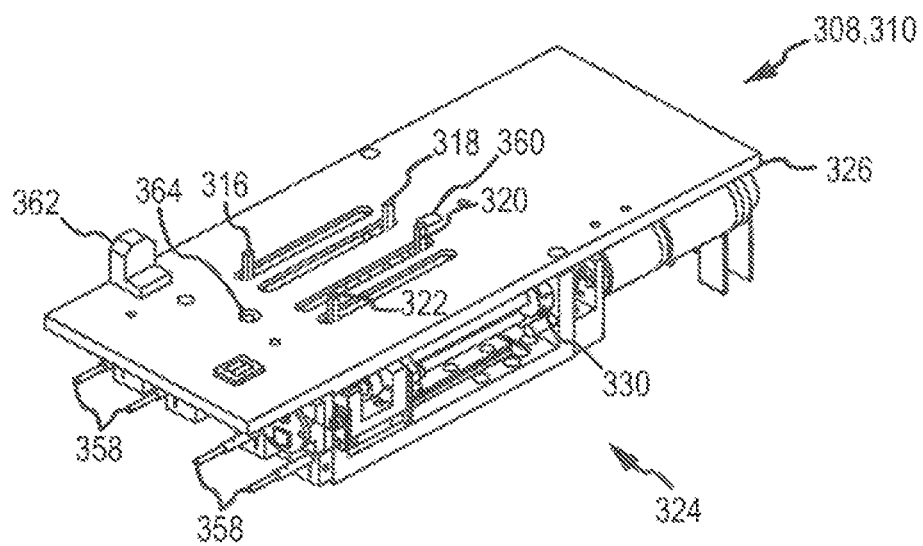
FIGS. 4a-4c are isometric views showing a sheath manipulation base of FIGS. 3a-3b in greater detail.
Figure 4B:
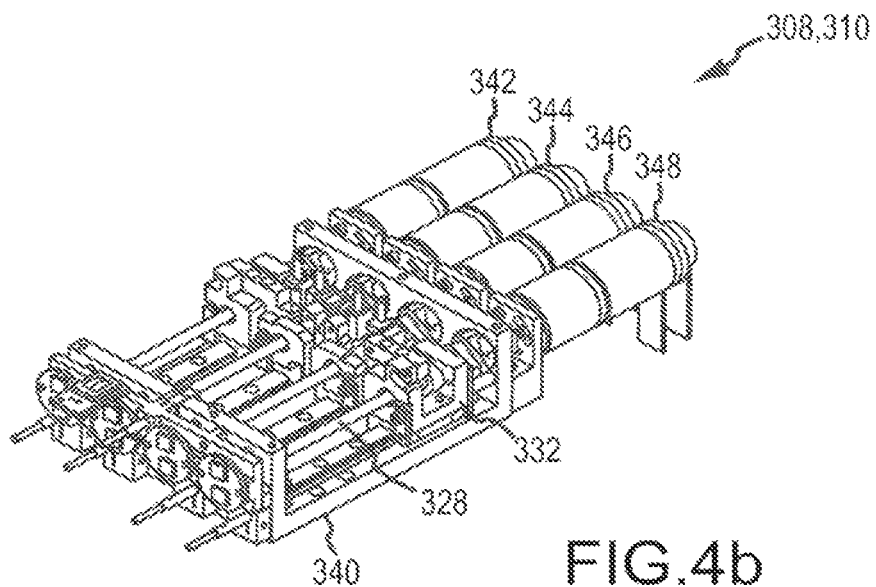
Figure 4C:
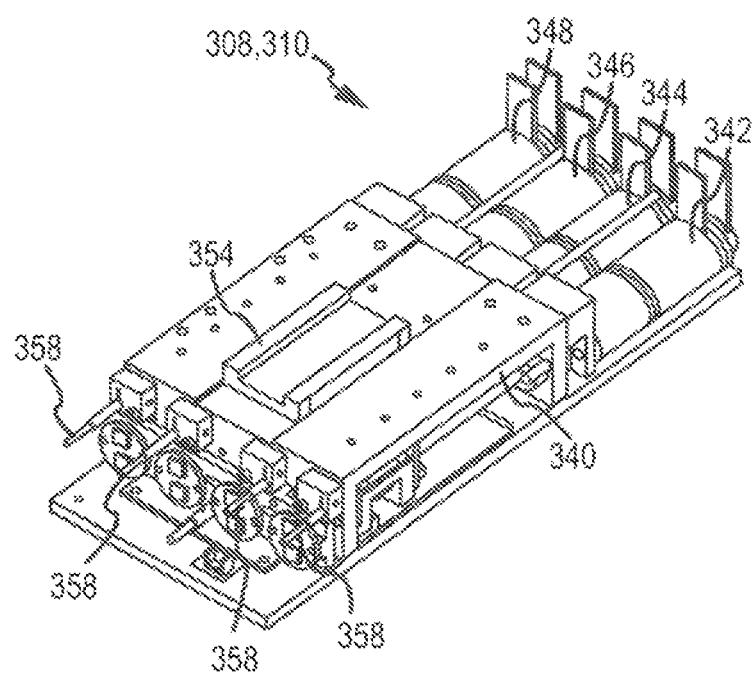
Figure 5A:
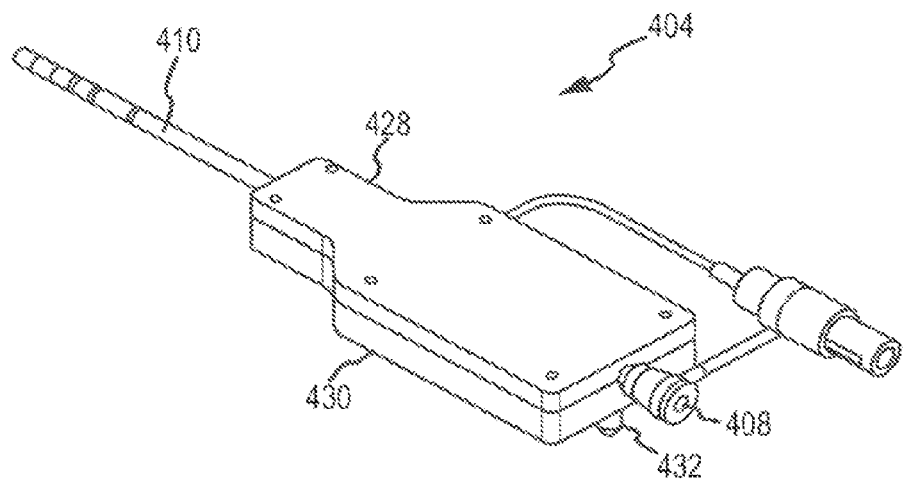
FIGS. 5a-5b are isometric views showing a sheath cartridge of FIGS. 3a-3b in greater detail.
Figure 5B:
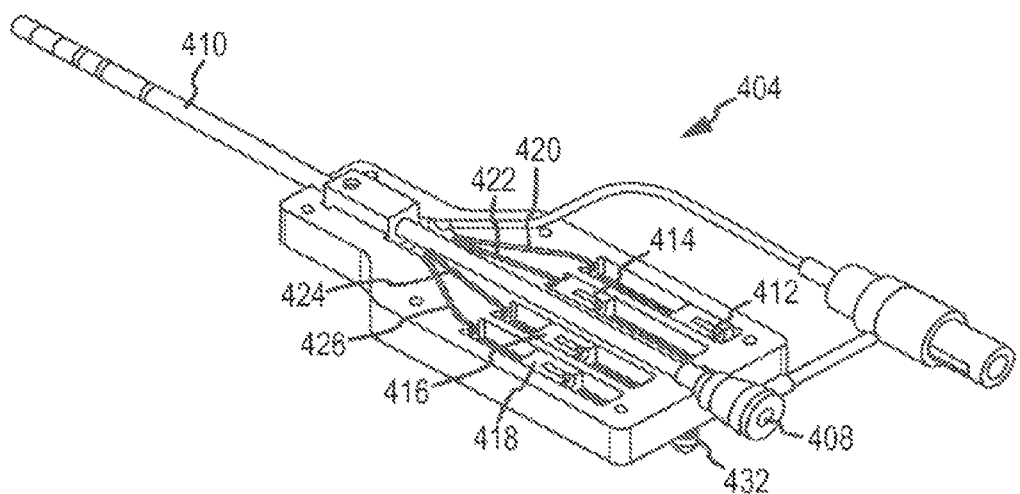

In the Figures to follow, FIGS. 3a-3b will show a manipulator assembly, FIGS. 4a-4c will show a manipulation base, and FIGS. 5a-5b will show a device cartridge.

FIG. 3a is an isometric view, with portions omitted for clarity, of manipulator assembly 302. Assembly 302 includes a catheter manipulator mechanism 304, a sheath manipulator mechanism 306, a catheter manipulation base 308, a sheath manipulation base 310, a first (catheter) drive mechanism 312, a second (sheath) drive mechanism 314, and a track 356. As further shown, assembly 302 further includes a catheter cartridge 402 and a sheath cartridge 404, with a catheter 406 having a proximal end opening 408 coupled to the catheter cartridge 402 and a sheath 410 coupled to the sheath cartridge 404.

Catheter and sheath manipulator mechanisms 304, 306 are configured to manipulate the several different movements of the catheter 406 and the sheath 410. First, each mechanism 304, 306 is configured to impart translation movement to the catheter 406 and the sheath 410. Translation movement here refers to the independent advancement and retraction (withdrawal) as shown generally in the directions designated D1 and D2 in FIG. 3a. Second, each mechanism 304, 306 is also configured to effect deflection of the distal end of either or both of the catheter and sheath 406, 410. Third, each mechanism 304, 306 can be operative to effect a so-called virtual (omni-directional) rotation of the distal end portion of the catheter 406 and the sheath 410. Virtual rotation, for example, can be made through the use of independent four-wire steering control for each device (e.g., eight total steering wires, comprising four sheath control wires and four catheter control wires). The distal end movement is referred to as "virtual" rotation because the outer surface of the sheath (or catheter) does not in fact rotate in the conventional sense (i.e., about a longitudinal axis) but rather achieves the same movements as conventional uni-planar deflection coupled with axial rotation. In addition to the present description of virtual rotation, further details can be found in PCT/US2009/038597 entitled "ROBOTIC CATHETER SYSTEM WITH DYNAMIC RESPONSE", published as WO 2009/120982.

Each manipulator mechanism 304, 306 further includes a respective manipulation base 308, 310 onto which are received catheter and sheath cartridges 402, 404. Each interlocking base 308, 310 can be capable of travel in the longitudinal direction of the catheter/sheath (i.e., D1, D2 respectively) along a track 356. In an embodiment, D1 and D2 can each represent a translation of approximately 8 linear inches. Each interlocking base 308, 310 can be translated by a respective high precision drive mechanism 312, 314. Such drive mechanisms can include, for example and without limitation, an electric motor driven lead screw or ball screw.

The manipulator mechanisms 304, 306 are aligned with each other such that catheter 406 can pass through sheath 410 in a coaxial arrangement. Thus, sheath 410 can include a water-tight proximal sheath opening 408. Overall, the manipulator mechanisms 304, 306 are configured to allow not only coordinated movement but also relative movement between catheter and sheath cartridges 402, 404 (and thus relative movement between catheter and sheath).

FIG. 3b is an isometric view of manipulator assembly 302, substantially the same as FIG. 3a except that catheter and sheath cartridges 402, 404 are omitted (as well as catheter and sheath 406, 410) so as to reveal an exposed face of the manipulation bases 308, 310.

FIG. 4a is an isometric, enlarged view showing manipulation base 308 (and base 310) in greater detail. Each cartridge 402, 404 has an associated manipulation base 308, 310. Each base 308, 310 can include a plurality of fingers 316, 318, 320 and 322 (e.g., one per steering wire) that extend or protrude upwardly to contact and interact with steering wire slider blocks (i.e., such as slider blocks 412, 414, 416, 418 are best shown in FIG. 5b) to independently tension select steering wires 420, 422, 424, 426 (also best shown in FIG. 5b). Each finger can be configured to be independently actuated (i.e., moved back and forth within the oval slots depicted in FIG. 4a) by a respective precision drive mechanism, such as a motor driven ball screw 324. A plate 326 provides a surface onto which one of the cartridges 402, 404 are seated.

FIG. 4b is an isometric, enlarged view of base 308 (and base 310), substantially the same as FIG. 4a except with plate 326 omitted. Each motor-driven ball screw 324 (best shown in FIG. 4a) i.e., for both finger control and for cartridge translation control, can further include encoders to measure a relative and/or an absolute position of each element of the system. Moreover, each motor-driven ball screw 324 (i.e., for both finger control and cartridge translation control) can be outfitted with steering wire force sensors to measure a corresponding steering wire tension. For example, a corresponding finger 316, 318, 320 or 322 can be mounted adjacent to a strain gauge for measuring the corresponding steering wire tension. Each motor-driven ball screw 324 can include a number of components, for example only, a rotary electric motor (e.g., motors 342, 344, 346 and 348), a lead screw 328, a bearing 330 and a coupler 332 mounted relative to and engaging a frame 340. In the depicted embodiments linear actuation is primarily, if not exclusively, employed. However, some known examples of systems with rotary-based device drivers include U.S. application Ser. No. 12/150,110 filed Apr. 23, 2008 (the '110 application); and U.S. application Ser. No. 12/032,639 filed Feb. 15, 2008 (the '639 application). The '110 application and the '639 application are hereby incorporated by reference in their entirety as though fully set forth herein. These and other types of remote actuation can directly benefit from the teaching of the instant disclosure.

FIG. 4c is an isometric, enlarged view of base 308 (and base 310) that is taken from an opposite side as compared to FIGS. 4a-4b. Bases 308, 310 can include components such as a plurality of electrically-operated motors 342, 344, 346 and 348, respectively coupled to fingers 316, 318, 320 and 322. A bearing 354 can be provided to facilitate the sliding of bases 308, 310 on and along track 356. A plurality of inductive sensors (e.g. home sensors) 358 can also be provided for guiding each manipulation base to a home position.

FIG. 5a is an isometric, enlarged view showing, in greater detail, sheath cartridge 404. It should be understood that the description of sheath cartridge 404, except as otherwise stated, applies equally to catheter cartridge 402. Catheter 406 and sheath 410 can be substantially connected or affixed to respective cartridges 402, 404 (e.g., in the neck portion). Thus, advancement of cartridge 404 correspondingly advances the sheath 410 and retraction of cartridge 404 retracts the sheath 410. Likewise, although not shown, advancement of cartridge 402 correspondingly advances catheter 406 while a retraction of cartridge 402 retracts catheter 406. As shown, sheath cartridge 404 includes upper and lower cartridge sections 428, 430.

FIG. 5b is an isometric, enlarged view showing, in greater detail, sheath cartridge 404, with upper section 428 omitted to reveal interior components. Cartridge 404 can include slider blocks (e.g., as shown for cartridge 404, slider blocks 412, 414, 416, 418), each rigidly and independently coupled to a respective one of a plurality of steering wires (e.g., sheath steering wires 420, 422, 424, 426) in a manner that permits independent tensioning of each steering wire. Likewise, cartridge 402 for catheter 406 also includes slider blocks for coupling to a plurality (i.e., four) steering wires. Device cartridges 402, 404 can be provided as a disposable item that is capable of being easily positioned (e.g., snapped) into place (i.e., onto a respective base 408, 410). Sheath cartridge 404 can be designed in a similar manner as the catheter cartridge 402, but will typically be configured to provide for the passage of catheter 406.

Referring to FIGS. 4a and 5a, catheter and sheath cartridges 402, 404 are configured to be secured or locked down onto respective manipulation bases 308, 310. To couple cartridge 402 (and 404) with base 308 (and 310), one or more locking pins (e.g., 432 in FIG. 5a) on the cartridge can engage one or more mating recesses 360 in the base (see FIG. 4a). In an embodiment, such recesses 360 can include an interference lock such as a spring detent or other locking means. In an embodiment, such other locking means can include a physical interference that can require affirmative/positive action by the user to release the cartridge. Such action can include or require actuation of a release lever 362. Additionally, the cartridge can include one or more locator pins (not shown) configured to passively fit into mating holes on the base (e.g., 364 in FIG. 4a).

In operation, a user first manually positions catheter 406 and sheath 410 (with catheter 406 inserted in sheath 410) within the vasculature of a patient. Once the medical devices are roughly positioned in relation to the heart or other anatomical site of interest, the user can then engage or connect (e.g., "snap-in") the catheter and sheath cartridges into place on respective bases 308, 310. When a cartridge is interconnected with a base, the fingers fit into the recesses formed in the slider blocks. For example, with respect to the sheath cartridge 404 and sheath base 310, each of the plurality of fingers 316, 318, 320 or 322 fit into corresponding recesses formed between the distal edge of slider blocks 412, 414, 416, 418 and a lower portion of the cartridge housing (best shown in FIG. 5b). Each finger can be designed to be actuated in a proximal direction to respectively move each slider block, thereby placing the respective steering wire in tension (i.e., a "pull" wire). Translation, distal end bending and virtual rotation can be accomplished through the use of the RCGS 10.

Figure 6:
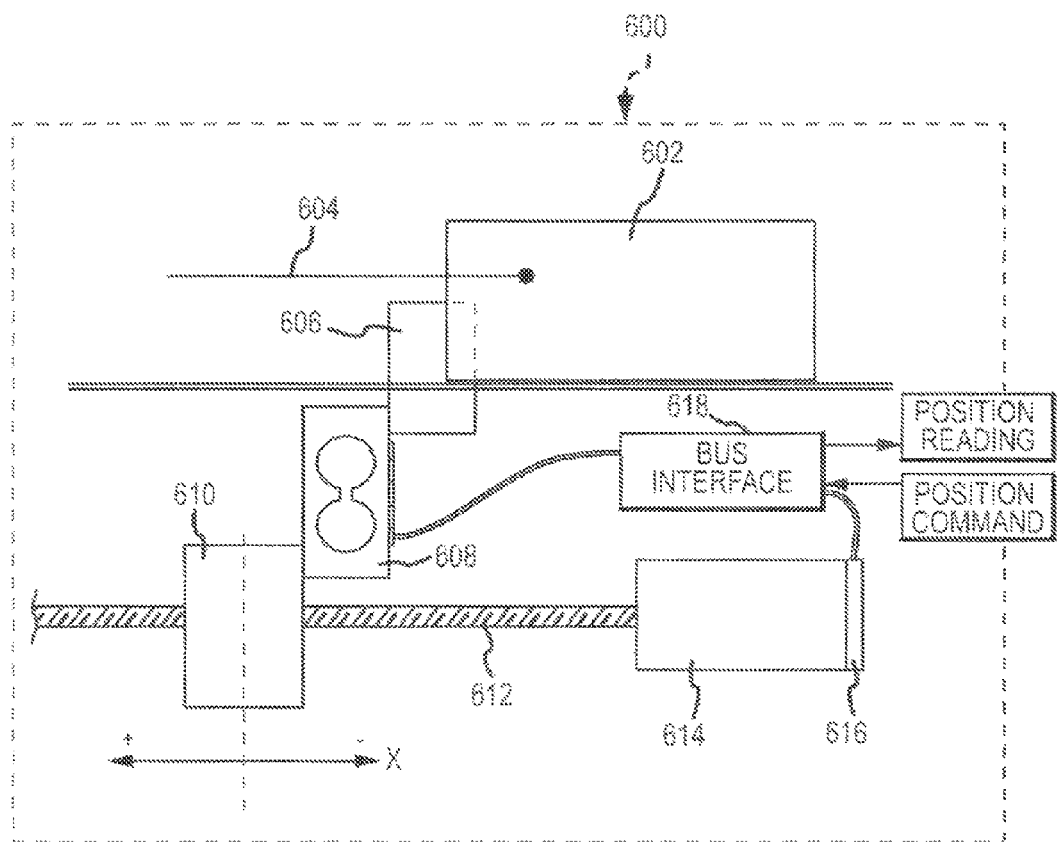
FIG. 6 is a diagrammatic view of the sheath manipulation mechanism of FIG. 2.

FIG. 6 is a diagrammatic view of a node suitable for connection to a communications bus (not shown) in RCGS 10. The node includes an actuation unit 600, similar to the actuation mechanisms described above (e.g., catheter actuation mechanism 304). The RCGS 10 can have at least ten such actuation units (i.e., one for each of the four catheter steering wires, four sheath steering wires, one catheter manipulation base and one sheath manipulation base), which as described include electric motors. The diagnostic logic of the present disclosure is configured to monitor all the electric motors to detect runaway motor fault conditions.

FIG. 6 shows in diagrammatic or block form many of the components described above—where appropriate, references to the earlier describe components will be made. Actuation unit 600 includes a first, slidable control member 602 (i.e., slider as described above) that is connected to or coupled with a second, tensile control member 604 (i.e., steering wire as described above). The slider 602 can be configured to interface with a third, movable control member 606 (i.e., finger as described above). The finger 606 can further be operatively coupled with a portion of a sensor 608 (e.g., a force sensor), which, in turn, can be coupled with a translatable drive element 610 that can be mechanically moved. For example, without limitation, translatable drive element 610 can ride on or can otherwise be mechanically moved by a mechanical movement device 612 that, in turn, can be coupled with an electric motor 614. The mechanical movement device 612 can comprise a lead screw while the translatable drive element 610 can comprise a threaded nut, which can be controllably translated by screw 612 in the X+ or X− directions. In another embodiment, mechanical movement device 612 can include a ball screw, while translatable drive element 610 can include a ball assembly. Many variations are possible, as will be appreciated by one of ordinary skill in the art.

Relevant to the diagnostic logic described herein, the actuation unit 600 also includes a rotary motor position encoder 616 that is coupled to the motor 614 and is configured to output a signal indicative of the position of the motor 614. The diagnostic logic is configured to process this sensed motor position relative to other available information, such as the target motor position, to detect the presence of motor runaway. The encoder 616 may comprise an internal, optical encoder assembly, integral with motor 614, configured to produce a relatively high accuracy output. The motor position sensor may operate in either absolute or relative coordinates. In an embodiment, a second motor position sensor (not shown) may also be provided, such as a potentiometer (or impedance-based), configured to provide a varying voltage output proportional to the motor's rotary position. The output of the secondary position sensor may be used as an integrity check of the operating performance of the primary position sensor (encoder) during start-up or initialization of the actuation unit.

Actuation unit 600 also includes one or more local controllers including a bus interface 618 to facilitate exchange of information between actuation unit 600 and electronic control system 200 (via the bus). The controller communicates with the main electronic control system 200 via the bus interface and is configured, among other things, to (1) receive and execute motor actuation commands issued by the electronic control system 200 for controlling the movements of motor 614; and (2) receive and execute a command (issued by the electronic control system 200) to take a motor position sensor reading, for example, from encoder 616 and subsequently report the reading to system 200.

Motor Runaway Automatic Detection/Prevention System.

With the description of an exemplary RCGS 10 given above, one of ordinary skill in the art will appreciate the need to monitor for and detect fault conditions indicative of motor runaway so as to prevent unexpected and perhaps undesirable catheter and/or sheath movements. In an embodiment, software routines programmed in the electronic control system 200 implement logic configured to monitor and detect such fault conditions, based on an assessment of (1) a sensed motor position; (2) a commanded motor position; as well as (3) a prescribed target motor position. When the diagnostic logic determines that any one of the motors is operating in a runaway fault condition, the logic will terminate or otherwise cause to terminate the needed operating power to the motors to thereby abate the runaway fault condition.

FIG. 7 is a block diagram showing electronic control system 200 of FIG. 1, in greater detail. The system 200 includes an electronic control unit (ECU) 202 having a processor 204 and an associated memory 206. The system 200 further includes logic, which in an embodiment may take the form of software stored in memory 206 and configured for execution by the processor 204. The ECU 202 may comprise conventional apparatus known in the art. Generally, the ECU 202 is configured to perform core operating functions of the RCGS 10 through a core operating module 208, and is further configured to perform diagnostic functions for monitoring, detecting and abating motor runaway through a diagnostic module 210. The core operating module 208 may include a user interface 212, an input and output module 214 and an operating control module 216.

The user interface 212 is configured to cooperate with the input control system 100 and display 12 described above (FIG. 1) to allow a user to interact with the RCGS 10, for controlling the movements of both the catheter 406 and the sheath 410. The input/output module 214 is configured to facilitate the input and output of data from sensors, data storage units, imaging systems and the like, as may be needed or desired to support the operation of the RCGS 10.

The operating control module 216 is configured to implement a predetermined operating control strategy (i.e., higher level control algorithms) for the RCGS 10. Generally, the operating control module 216 is configured to receive user inputs as well as other inputs (e.g., catheter tip position, sensed motor positions, etc.) and output actuation control signals 218 (e.g., motor actuation commands) to achieve the desired movements (i.e., sheath and/or catheter translation, sheath and/or catheter deflection or virtual rotation). A plurality of electrically-operated actuation units, such as a plurality of electric motors (i.e., motors $614_1$, $614_2$, ... $614_n$) like in FIG. 6, are in communication with ECU 202 and are configured to (1) receive the actuation control signals 218 from ECU 202 as well as (2) provide sensed motor position readings 230 back to ECU 202 for both control as well as diagnostic purposes.

FIG. 8 is a block diagram showing a high level function performed by the operating control module 216. Block 220 represents the desired movements of the medical device as specified by the user via the input control system 100/user interface 212, or as otherwise determined or limited by the operating control module. For example, the prescribed target position for any motor may be calculated by the operating control 216 depending upon the type of motion (e.g., deflection, rotation, and translation), for each and every axis of the motors (e.g., 10 motors in the exemplary RCGS 10). The operating control 216, after making the above determinations, outputs the needed motor movements to move each motor from its current position to the calculated target position. The ECU 202 (operating control 216) is further configured to produce the actuation control signals 218 in a form suitable as a motor actuation command, to control the target motor to make the desired/commanded movements (e.g., direction, counts). In a Controller Area Network (CAN) bus embodiment, the ECU 202 may issue synchronous commands addressed to the several motor nodes (e.g., FIG. 6) calling for the motors to move to the target positions, which commands are then "actuated on" by the nodes when the main ECU 202 subsequently issues a so-called synchronization (SYNC) command. This approach is particularly useful since it results in coordinated motor movements from all the motors that need to be all occurring at substantially the same time.

Diagnostic module 210 is configured to monitor the operation of the electric motors $614_1$, $614_2$, ..., $614_n$ and detect when a predetermined fault condition associated with at least one of the motors occurs. The diagnostic module 210 includes a monitoring module 224, a motor runaway fault condition detection module 226 and fault condition abatement (or prevention) module 228. The monitoring module 224 implements continuous monitoring of the electric motors, and obtains sensed motor position readings based on a so-called I/O cycle, as illustrated in FIG. 9.

Figure 9:
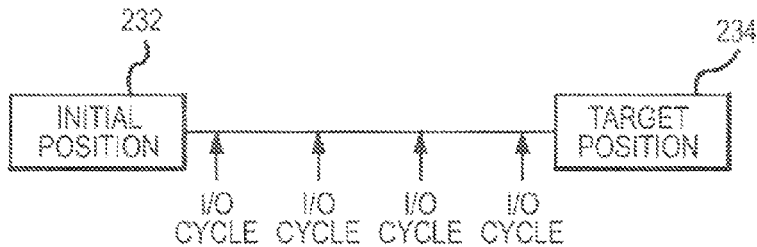
FIG. 9 is a block diagram view of a motor movement between an initial position and a target position, with periodic monitoring by the diagnostic logic of FIG. 7 for motor runaway fault conditions every input/output (I/O) cycle.

FIG. 9 is a simplified diagram showing the substantially continuous monitoring implemented by monitoring module 224. The monitoring module 224 obtains and assesses motor position readings 230 in accordance with the I/O cycle. In an embodiment, the RCGS 10 operates in accordance with a system wide input/output cycle, which may be on the order of between about 30-50 milliseconds, and may be about 50 milliseconds. The I/O cycle is the "heartbeat" of the RCGS 10, establishing a timing reference for a variety of functions, including diagnostic module 210 (for motor runaway). With reference to a particular example in FIG. 9, during each I/O cycle as the motor travels from an initial position 232 to a target position 234, the monitoring module 224 obtains and processes fresh (updated) motor position readings. In a Controller Area Network (CAN) bus embodiment, the ECU 202 may issue synchronous commands addressed to the several motor nodes (e.g., FIG. 6) to obtain a motor position reading, which are then "actuated on" by the nodes when the main ECU 202 subsequently issues a so-called synchronization (SYNC) command. This approach is particularly useful since it results in sensed motor readings from all the motors taken all at substantially the same time, facilitating the system wide control of the motors. This deterministic approach assures that any motor runaway fault condition that may occur will not go undetected for any more than one I/O cycle's worth of time.

Returning to FIG. 7, diagnostic module 210 further includes detection module 226 configured to use the sensed motor position readings 230 from monitoring module 224 to identify the presence of any one of a plurality of different fault conditions. The fault conditions may include: (i) a first condition when at least one of the motors rotate in a direction opposite that of a commanded direction ("wrong direction"); (ii) a second condition when at least one of the motors has rotated to an actual position short of or beyond a commanded position by at least a predetermined amount ("undershoot" or "overshoot" condition); (iii) a third condition when a rotational speed of at least one of the motors exceeds a respective maximum speed threshold ("overspeed" condition); and (iv) a fourth condition when a rate of change of the rotational speed of at least one of the motors exceeds a respective maximum acceleration threshold ("over-acceleration" condition). It should be understood that other fault conditions may be monitored for and detected.

Diagnostic module 210 further includes a fault condition abatement module 228 configured to abate or otherwise mitigate the fault condition and thus prevent or otherwise mitigate undesired and/or unexpected catheter and/or sheath movement. The logic implemented in fault abatement module 228 is configured to cooperate with external hardware to terminate operating power to the electric motors when a fault condition is detected. In this regard, the RCGS 10 may include a watchdog timer 236 or the like. Watchdog timer 236 is configured to have a countdown time interval which counts down (or up if so configured). The ECU 202 is configured to periodically set (or reset) timer 236, for example, using a timer set (or reset) signal 238. For example, this may occur every I/O cycle. The timer 236, which is coupled to a controlled power source 240, is configured to automatically generate a power termination signal 242 when the countdown time interval expires. The power source 240, in response to the power termination signal 242, will discontinue or terminate operating power 244 that is being provided to the electric motors. It should be understood that while timer 236 and power source 240 are shown separately, they may be integrated into a single unit.

To prevent the watchdog timer from terminating power, the ECU 202 is programmed (e.g., in a operating control routine) to assert, at times less than the countdown time interval, the set (or reset) signal 238 in order to refresh the countdown time interval. Through the foregoing arrangement, the watchdog timer 236 will automatically shut off the power to the system unless the system specifically confirms (e.g., through the periodic assertion of the refresh signal 238) that it is operating normally. However, when the detection module 226 detects a fault condition, the condition abatement module 228 suppresses or inhibits the ECU 202 from asserting the refresh signal 238, thereby allowing the countdown time interval to expire, thereby automatically terminating operating power to the motors. It should be understood that other mechanisms, including software, hardware, or combinations thereof, may by employed to cut power to the electric motors or to otherwise abate a detected motor runaway fault condition.

Figure 10:
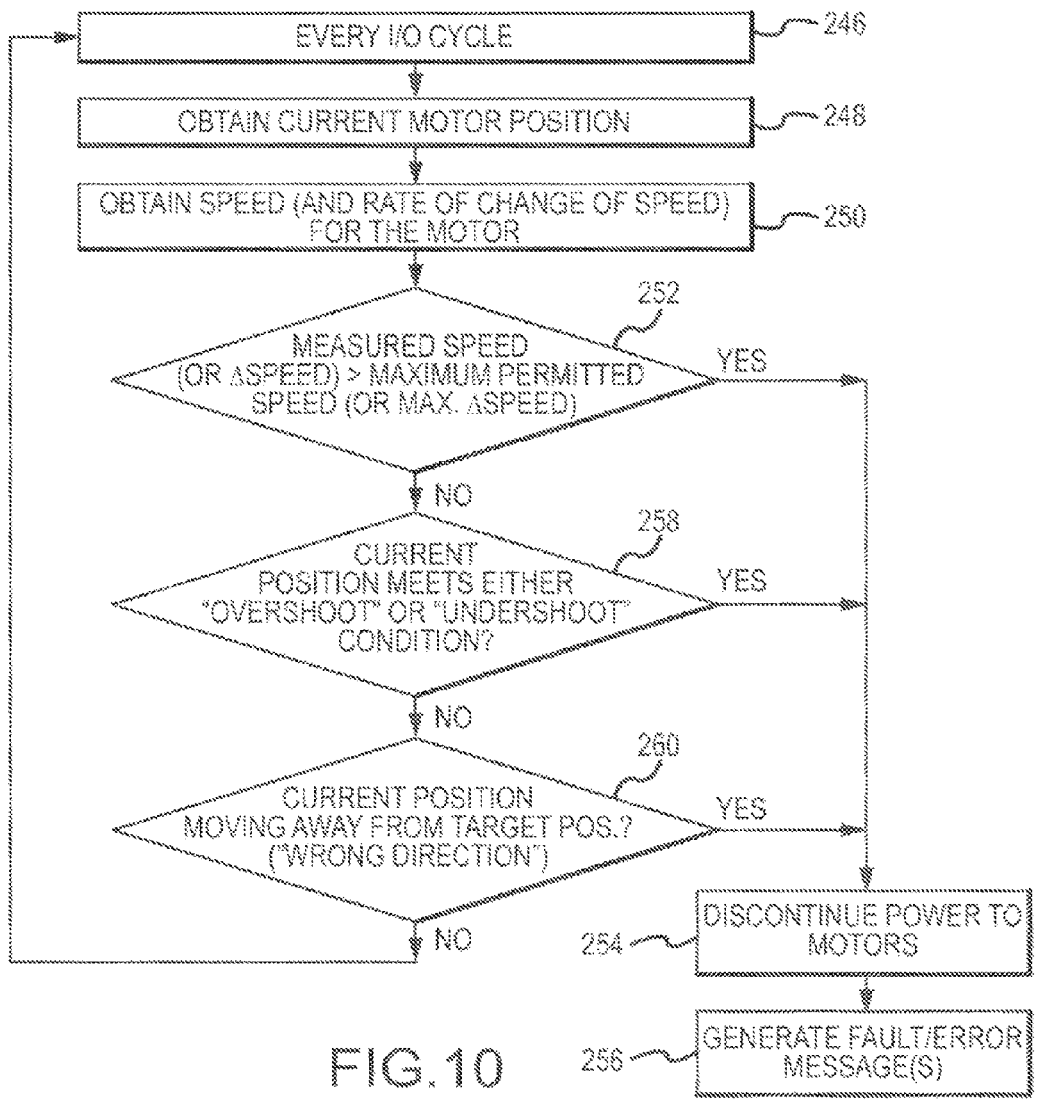
FIG. 10 is a flowchart diagram showing, in greater detail, the monitoring, detection and fault abatement functions shown in FIG. 8.
Figure 11:
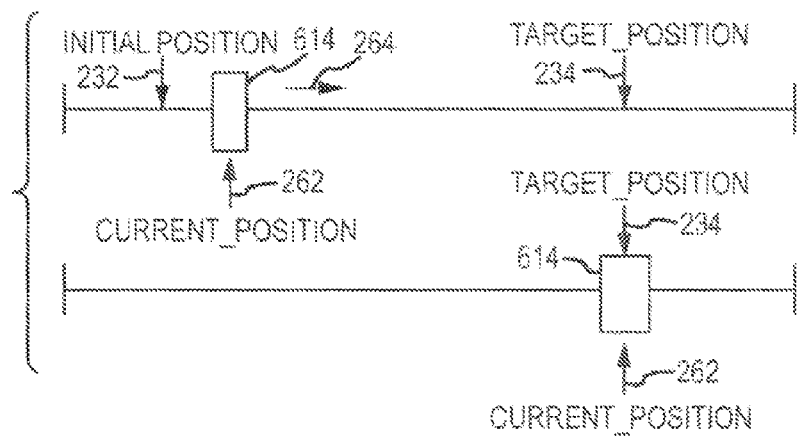
FIGS. 11-13 are motor position versus time diagrams illustrating a normal condition, an overshoot condition and a "wrong" direction condition, respectively.
Figure 12:
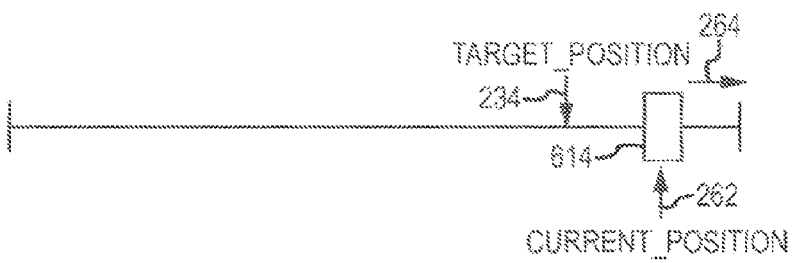
Figure 13:
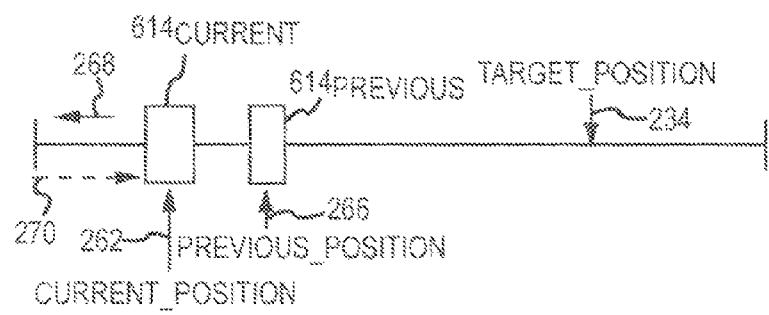

FIG. 10 is a flowchart showing a method of monitoring, detecting and abating a motor runaway fault condition. Reference will also be made to FIGS. 11-13 to illustrate particular normal and fault conditions. The sensed, current motor position of a particular motor will be referred to as "C", while the commanded, target motor position for that particular motor will be referred to as "T". When a target position T is requested, the current position will approach the target position (i.e., C approaches T). A predetermined tolerance (i.e., threshold, $\Delta$) is defined at the time the RCGS 10 is designed and corresponds to a maximum variance in the motor position allowed by the diagnostic logic before a runaway fault condition is deemed to have occurred. The predetermined tolerance may be selected based on system performance criteria (e.g., how much "play" in the system due to tolerances) as well as a function of the maximum speed of the motors ("stopping distance"). The predetermined tolerance, while configurable, is preferably not user configurable in an embodiment nor is it dynamically changing during the operation of RCGS 10. For the examples of FIGS. 11-13, assume that T>C at the time the target motor position is commanded. The logic presented below may be reversed when T<C.

The method begins in step 246, which indicates that the method is performed at no less than a predetermined time interval. In an embodiment, that time interval is the system I/O cycle time, although other time intervals may be suitable depending on the particular configuration of the RCGS. The method proceeds to step 248.

In step 248, the diagnostic module 210, in particular the monitoring module 224, obtains, for each actuation unit (motor) being monitored, a respective, current (updated) motor position ("C"). As described above, the motor position may be obtained from the position sensors on the motors. The method proceeds to step 250.

In step 250, the monitoring module 224, for each actuation unit (motor) being monitored, obtains or otherwise calculates a respective, current motor speed, as well as a respective, current rate of change of motor speed (acceleration). The diagnostic module 210 may be configured to obtain these parameters from the core operating logic 208, which may store these values for its own use. The method proceeds to step 252.

In step 252, the detection module 226 begins a sequence of several checks to determine whether one of the several conditions indicative of motor runaway exists. By way of example, FIG. 11 shows fault-free operation of an electric motor, with motor 614 moving between an initial position 232 and a target position 234 (T). The motor 614 has a current position 262 (C), which for purposes of description will be the updated position reading 230 obtained by the monitoring module each time the method loops (I/O cycle). The correct direction 264 is shown, which in the example of FIG. 11 happens to agree with the movement of the motor 614 (i.e., away from its initial position 232 and toward its target position 234). FIG. 11 also shows the motor 614 after it has reached its target position 234. As shown, the current position 262 ("C") is substantially the same as the target position 234, to within a predetermined threshold amount ($\Delta$), as set forth below:

$$C = T \pm \Delta$$

There is there neither undershoot nor overshoot. The foregoing outcome is the expected outcome when the motor does not experience a motor runaway fault condition.

With continued reference to step 252, the detection module 226 determines, for each actuation unit (motor), whether a respective current speed exceeds a predetermined maximum speed threshold or whether a respective current rate of change of speed exceeds a predetermined maximum acceleration threshold ("Over-speed" or "Over-acceleration" fault conditions). Values for the predetermined maximum speed and acceleration thresholds (for each motor) may be predetermined and available to the diagnostic module 210 (i.e., predetermined and stored in memory). If the answer is YES (speed or acceleration fault), then a fault has been detected and the method branches to steps 254 and 256 (described below). If the answer is NO, however, the method proceeds to step 258 for further checks.

In step 258, the detection module 226 determines, for each actuation unit (motor), whether a respective, current position (C) is short of ("Undershoot") or is greater than ("Overshoot") a respective target position (to within the predetermined threshold (tolerance)). The prescribed target position (for each motor) may be obtained from the core operating logic memory. As shown in FIG. 12 for an overshoot condition, the motor 614 is moving in a correct direction 264; however, the motor did not stop at the target position, but rather went past the target position ("Overshoot"). Accordingly, the motor's current position 262 (C) is greater than its target position 234 (T) by more than a predetermined threshold, as expressed below:

$$C > T \pm \Delta \text{ ("Overshoot")}$$

Although the undershoot condition is not shown, in that case, the motor 614 may also move in the correct direction 264 but settle in on a current position that is short of the target position. To ensure that the undershoot condition is not inadvertently detected merely because the motor passes through a position that would be considered "short of" the target, the detection logic must first confirm that the motor has stopped moving (e.g., by comparing the current position with an immediately previous current position, and if they are substantially the same, then the logic can conclude that the motor has stopped moving). Accordingly, provided the predicate condition is met (i.e., the motor has stopped moving), the motor's current position 262 (C), in an undershoot condition, will be less than its target position 234 (T), to within the predetermined threshold (tolerance), as expressed below $$C < T \pm \Delta \text{ ("Undershoot")}$$

If the answer is YES ("Undershoot" or "Overshoot"), then a fault has been detected and the method branches to steps 254 and 256. Otherwise, if the answer is NO, then the method proceeds to step 260 for more checks.

In step 260, the detection module 226 determines, for each actuation unit (motor), whether the motor is moving in the "wrong" direction (i.e., opposite that of the commanded direction). The detection module 226 first determines a direction 268 by comparing the current motor position ($614_{CURRENT}$) and a previous in time motor position ($614_{PREVIOUS}$). The module 226 then compares the actual direction of movement 268 with the commanded direction of movement 270. In effect, if successive current motor positions indicate that the motor is moving away from (rather than toward) the target position 234 (to within the predetermined threshold (tolerance)), then module 226 will detect a fault. This condition may be recognized as follows, using the above nomenclature:

$$C < C(\text{Previous}) \pm \Delta$$

Thus, if the answer is YES, then a fault has been detected and the method branches to steps 254 and 256. Otherwise, if the answer is NO, then the method will loop back to step 246 and wait until the next predetermined time to perform the fault detection (i.e., the next I/O cycle in the illustrative embodiment).

Steps 254, 256 perform fault abatement and user notification functions. In step 254, the fault abatement module 228 terminates operating power to the actuation units (motors), in the manner described above, for example only. The method then proceeds to step 256.

In step 256, the method generates a fault notification or error message to the user. In an embodiment, this fault notification may be audible, visual, tactile, haptic or in other ways now known or hereafter developed. In an embodiment, the diagnostic module 210 generates a user perceptible mechanism through which the RCGS 10 solicits an acknowledgement from the user, in effect, that he/she recognizes that an actuation unit (motor) fault has occurred, and optionally, that appropriate action in response to the fault has been taken. In this embodiment, the RCGS 10 is further configured to inhibit operation or at least predetermined functionality of the RCGS 10 until the system-solicited user input/recognition has been obtained (i.e., user intervention required for a motor runaway fault).

In sum, in order to automatically detect a runaway fault condition, the diagnostic module 210 relies on knowledge of the current position of the motors as well as the prescribed target position for the motors. In turn, the prescribed target position of any motor may be calculated by the core operating logic 208 depending upon the type of motion (e.g., deflection, rotation, and translation), for each and every axis of the motors (e.g., 10 motors in the exemplary RCGS 10). The motors are actuated by the core operating logic 208 to move to the prescribed target position and the intermediate positions of each motor are monitored by the diagnostic logic 210 to determine the amount of overshoot, undershoot, direction of movement and maximum number of counts of travel in the prescribed direction. In addition, the speed and rate of change of speed is also monitored to detect any anomalies. The diagnostic logic 210 performs monitoring and comparison (i.e., detection of fault conditions) during each and every I/O cycle to ensure the integrity of the RCGS 10. When a motor runaway fault condition is detected by the diagnostic logic 210, the operating power to the electric motors is terminated and a notification (e.g., an emergency message) is generated to alert the physician or operator.

The detection and abatement logic is advantageously implemented in ECU 202 under software control wherein the abatement, namely terminating operating power to the motors, is also initiated under software control. The foregoing approach minimizes the number of external hardware components needed to detect the motor runaway fault conditions and abate the fault. Moreover, the software is configurable such that a wide range of values may be specified for all the parameters described above (i.e., maximum prescribed motor speed, maximum prescribed motor acceleration, etc.).

The foregoing system enhances the experience of the electrophysiologist (EP) by providing additional safeguards within the RCGS 10. The diagnostic capabilities described herein also enhance the safety of the patient so that only intended movements of the catheter and sheath occur.

It should be understood that while the RCGS 10 as described herein employed linear actuation (i.e., fingers, slider blocks), the spirit and scope of the inventions contemplated herein is not so limited and extends to and covers, for example only, a manipulator assembly configured to employ rotary actuation of the control members. In further embodiments, the ECU may be configured to cause the manipulator assembly to either linearly actuate and rotary actuate one or more control members associated with the medical device for at least one of translation, rotation, virtual rotation and deflection movement.

Of course, additional apparatus may be incorporated in or used in connection with the RCGS 10, whether or not illustrated in FIG. 1. For example, the following may be coupled (directly or indirectly) to RCGS 10 or used in connection with RCGS 10, depending on the particular procedure: (1) an electrophysiological (EP) monitor or display such as an electrogram signal display; (2) one or more body surface electrodes (skin patches) for application onto the body of a patient (e.g., an RF dispersive indifferent electrode/patch for RF ablation); (3) an irrigation fluid source (gravity feed or pump); and (4) an RF ablation generator (e.g., such as a commercially available unit sold under the model number IBI-1500T RF Cardiac Ablation Generator, available from St. Jude Medical, Inc.). To the extent the medical procedure involves tissue ablation (e.g., cardiac tissue ablation), various types of ablation energy sources (i.e., other than radio-frequency—RF energy) may be used in by a catheter manipulated by RCGS 10, such as ultrasound (e.g. high-intensity focused ultrasound (HIFU)), laser, cryogenic, chemical, photo-chemical or other energy used (or combinations and/or hybrids thereof) for performing ablative procedures.

Further configurations, such as balloon-based delivery configurations, may be incorporated into catheter embodiment consistent with the invention. Furthermore, various sensing structures may also be included in the catheter, such as temperature sensor(s), force sensors, various localization sensors (see description above), imaging sensors and the like.

As used herein, "distal" refers to an end or portion thereof that is advanced to a region of interest within a body (e.g., in the case of a catheter or sheath) while "proximal" refers to the end (or portion thereof) that is opposite of the distal end, and which may be disposed outside of the body and manipulated, for example, automatically through RCGS 10.

It should be understood that an electronic controller or ECU as described above for certain embodiments may include conventional processing apparatus known in the art, capable of executing pre-programmed instructions stored in an associated memory, all performing in accordance with the functionality described herein. To the extent that the methods described herein are embodied in software, for example the diagnostic methods for detecting and abating motor runaway, the resulting software may be stored in an associated memory and may also constitute the means for performing such methods. Implementation of certain embodiments of the invention, where done so in software, would require no more than routine application of programming skills by one of ordinary skill in the art, in view of the foregoing enabling description. Such an electronic control unit or ECU may further be of the type having both ROM, RAM, a combination of non-volatile and volatile (modifiable) memory so that the software can be stored and yet allow storage and processing of dynamically produced data and/or signals.

It should be further understood that an article of manufacture in accordance with this disclosure includes a computer-readable storage medium having a computer program encoded thereon for implementing the motor runaway detection and abatement methods described herein. The computer program includes code to perform one or more of the methods disclosed herein.

Although a number of embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An apparatus for use in a robotic control system configured to manipulate a medical device, comprising:
   an electronic control unit (ECU) and a memory coupled to said ECU; and
   logic stored in said memory configured to be executed by said ECU, said logic including a diagnostic module;
   said diagnostic module being configured to monitor operation of a plurality of electrically-operated actuation units of the robotic control system during the time that at least one of said actuation units is moving according to actuation control signals so as to manipulate the medical device in accord with a user input indicative of a desired movement of the medical device, said diagnostic module being configured to detect when a predetermined fault condition associated with at least one of said actuation units occurs, said diagnostic module being further configured to output a fault notification associated with said fault condition, wherein said diagnostic module is configured to generate a user-perceptible mechanism through which an input from the user is solicited after said predetermined fault condition has been detected, wherein said user-perceptible mechanism is configured to obtain said input from the user and wherein said input is indicative of user-recognition of the occurrence of said predetermined fault condition, and wherein said logic is further configured to inhibit operation or at least predetermined functionality of said robotic control system until said input indicative of said user recognition has been obtained.

2. The apparatus of claim 1 wherein said diagnostic module is further configured to cause operating power provided to said actuation units to be terminated when said predetermined fault condition is detected to thereby abate said fault condition.

3. The apparatus of claim 2 further comprising a watchdog timer having a countdown time interval, said timer being configured to terminate operating power to said actuation units when said countdown time interval expires, said logic being further configured to reset said watchdog timer at time periods less than said countdown time interval, said diagnostic module being configured to inhibit said logic from resetting said timer when said predetermined fault condition has been detected.

4. The apparatus of claim 1 wherein said actuation units comprise electric motors, and wherein said predetermined fault condition is selected from the group comprising (i) a first condition when at least one of said motors rotate in a direction opposite that of a commanded direction; (ii) a second condition when at least one of said motors has rotated to an actual position short of or beyond a commanded position by at least a predetermined amount; (iii) a third condition when a rotational speed of at least one motor exceeds a respective maximum speed threshold; and (iv) a fourth condition when a rate of change of said rotational speed of at least one motor exceeds a respective maximum acceleration threshold.

5. The apparatus of claim 1 wherein said diagnostic module is configured to detect said first and said second conditions based on at least a motor position.

6. The apparatus of claim 1 wherein said medical device is one of a catheter and a sheath.

7. The apparatus of claim 1 wherein said fault notification is a user-perceivable fault notification.

8. The apparatus of claim 1 wherein said logic is further configured to produce a user interface to facilitate interaction between said apparatus and a user.

9. The apparatus of claim 1 wherein said input further indicates that the user has taken appropriate action in response to said predetermined fault condition.

10. A robotic control and guidance system for manipulating a medical device, comprising:
    an electronic control unit (ECU), a memory coupled to said ECU, and logic stored in said memory configured to be executed by said ECU, said logic including an operating module and a diagnostic module;
    a manipulator assembly including a plurality of electrically-operated actuation units configured to actuate one or more control members of the medical device in response to a plurality of actuation control signals;
    said operating module being configured to produce said actuation control signals so as to manipulate the medical device in accordance with a predetermined operating strategy and in accord with a user input indicative of a desired movement of the medical device;
    said diagnostic module being configured to monitor operation of said actuation units during the time that at least one of said actuation units is moving according to said actuation control signal, said diagnostic module being configured to detect when a predetermined fault condition occurs, said diagnostic module being further configured to output a fault notification associated with said predetermined fault condition, wherein said diagnostic module is configured to generate a user-perceptible mechanism through which an input from the user is solicited after said predetermined fault condition has been detected, wherein said user-perceptible mechanism is configured to obtain said input from the user and wherein said input is indicative of user-recognition of the occurrence of said predetermined fault condition, wherein said logic is further configured to inhibit operation or at least predetermined functionality of said robotic control system until said input indicative of said user recognition has been obtained.

11. The system claim 10 wherein said diagnostic module is further configured to cause operating power provided to said actuation units to be terminated when said predetermined fault condition is detected to thereby abate said fault condition.

12. The system of claim 11 further comprising a watchdog timer having a countdown time interval, said timer being configured to terminate operating power to said actuation units when said countdown time interval expires, said logic being further configured to reset said watchdog timer at time periods less than said countdown time interval, said diagnostic module being configured to inhibit said logic from resetting said watchdog timer when said predetermined fault condition has been detected.

13. The system of claim 10 wherein said actuation units comprise electric motors, and wherein said predetermined fault condition is selected from the group comprising (i) a first condition when at least one of said motors rotate in a direction opposite that of a commanded direction; (ii) a second condition when at least one of said motors has rotated to an actual position short of or beyond a commanded position by at least a predetermined amount; (iii) a third condition when a rotational speed of at least one motor exceeds a respective maximum speed threshold; and (iv) a fourth condition when a rate of change of said rotational speed of at least one motor exceeds a respective maximum acceleration threshold.

14. The apparatus of claim 10 wherein said input further indicates that the user has taken appropriate action in response to said predetermined fault condition.

15. A method of operating a robotic control and guidance system configured to manipulate a medical device, comprising:
(A) determining, using an electronic control unit (ECU), actuation control signals in accordance with a predetermined operating strategy;
(B) operating a plurality of electrically-operated actuation units based on the actuation control signals so as to actuate one or more control members of the medical device, thereby manipulating the medical device in accord with a user input indicative of a desired movement of the medical device;
(C) monitoring the operation of the actuation units during the time that at least one of the actuation units is moving in response to the actuation control signals to detect a predetermined fault condition;
(D) outputting, when a predetermined fault condition associated with the actuation control units is detected, a fault notification associated with the detected predetermined fault condition,
(E) soliciting and obtaining an input from a user after the predetermined fault condition has been detected wherein said input is indicative of user-recognition of the fault condition; and
(F) inhibiting operation of the robotic system until the solicited user input has been obtained.

* * * * *